United States Patent
Laurent et al.

(10) Patent No.: US 6,251,378 B1
(45) Date of Patent: *Jun. 26, 2001

(54) PROCESS FOR DECREASING THE DEGRADATION OF THE COLOR OF OXIDATION DYED KERATIN FIBERS

(75) Inventors: Florence Laurent, Asniéres; Damarys Braida-Valerio, Paris, both of (FR)

(73) Assignee: L'Oreal, Paris (FR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/051,890
(22) PCT Filed: Oct. 3, 1996
(86) PCT No.: PCT/FR96/01547
 § 371 Date: Jun. 9, 1998
 § 102(e) Date: Jun. 9, 1998
(87) PCT Pub. No.: WO97/15271
 PCT Pub. Date: May 1, 1997

(30) Foreign Application Priority Data

Oct. 20, 1995 (FR) .................................................. 95 12385

(51) Int. Cl.$^7$ .............................. A61K 7/06; A61K 7/13
(52) U.S. Cl. ...................... 424/70.1; 424/70.11; 424/401; 8/405; 8/406; 8/408
(58) Field of Search .............................. 424/70.17, 70.11, 424/70.27, 70.28, 401; 8/405, 406, 408

(56) References Cited

U.S. PATENT DOCUMENTS

| | | | |
|---|---|---|---|
| 4,295,848 | * | 10/1981 | Grollier et al. . |
| 5,618,523 | | 4/1997 | Zysman et al. ..................... 424/70.1 |
| 5,700,456 | * | 12/1997 | Dubief et al. . |

FOREIGN PATENT DOCUMENTS

| | | |
|---|---|---|
| 2 359 399 | 6/1975 | (DE) . |
| 3 843 892 | 6/1990 | (DE) . |
| 4 133 957 | 4/1993 | (DE) . |
| 4 402 929 | 6/1995 | (DE) . |
| 4 420 736 | 8/1995 | (DE) . |
| 4 424 530 | 1/1996 | (DE) . |
| 4 424 533 | 1/1996 | (DE) . |
| 0 227 994 | 7/1987 | (EP) . |
| 0 278 505 A2 | 8/1988 | (EP) . |
| 0 278 505 B1 | 8/1988 | (EP) . |
| 0 500 437 | 8/1992 | (EP) . |
| 0 646 572 | 4/1995 | (EP) . |
| 0 647 617 | 4/1995 | (EP) . |
| 0 736 522 | 10/1996 | (EP) . |
| 2 586 913 | 3/1987 | (FR) . |
| 2 673 179 | 8/1992 | (FR) . |
| 2 679 770 | 2/1993 | (FR) . |
| 2 718 960 | 10/1995 | (FR) . |
| 63-169571 | 7/1988 | (JP) . |
| 94/07844 | 4/1994 | (WO) . |
| 94/08969 | 4/1994 | (WO) . |
| 94/08970 | 4/1994 | (WO) . |
| 94/10131 | 5/1994 | (WO) . |
| 94/24097 | 10/1994 | (WO) . |
| 95/16665 | 6/1995 | (WO) . |
| 95/23807 | 9/1995 | (WO) . |

OTHER PUBLICATIONS

Zviak, The Science of Hair Care, pp. 263–286, 1986.*
English Language Derwent Abstract of EP 0 647 617.
English Language Derwent Abstract of FR 2 679 770.
English Language Derwent Abstract of FR 2 718 960.

(List continued on next page.)

Primary Examiner—Thurman K. Page
Assistant Examiner—Brian K. Seidleck
(74) Attorney, Agent, or Firm—Finnegan, Henderson, Farabow, Garrett & Dunner, L.L.P.

(57) ABSTRACT

The invention relates to a process for improving the color fastness of a dyed keratin fiber comprising applying to said fiber (a) at least one dye composition containing, in a medium suitable for dyeing, at least one oxidation base selected from bis(phenyl)alkylenediamines, para-aminophenols, ortho-aminophenols, heterocyclic bases and para-phenylenediamines of formula (I), and the addition salts of these compounds with an acid:

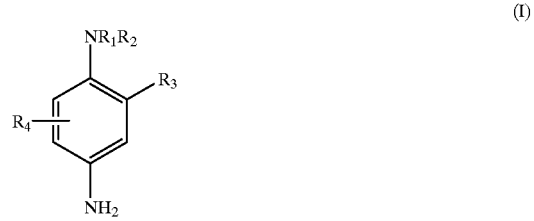

(I)

in which:

$R_1$ represents a hydrogen atom or a $C_1$–$C_4$ alkyl, $C_1$–$C_4$ monohydroxyalkyl, $C_2$–$C_4$ polyhydroxyalkyl, phenyl or 4'-aminophenyl radical, $R_2$ represents a hydrogen atom or a $C_1$–$C_4$ alkyl, $C_1$–$C_4$ monohydroxyalkyl or $C_2$–$C_4$ polyhydroxyalkyl radical, $R_3$ represents a hydrogen atom, a halogen atom, or a $C_1$–$C_4$ alkyl, $C_1$–$C_4$ monohydroxyalkyl or $C_1$–$C_4$ hydroxyalkoxy radical, and $R_4$ represents a hydrogen atom or a $C_1$–$C_4$ alkyl radical, and (b) developing the color at acidic, neutral or alkaline pH using an oxidizing agent, wherein said oxidizing agent is added to said dye composition at the time of use or is present in an oxidizing composition applied simultaneously or sequentially in a separate manner from said dye composition, wherein said dye composition, said oxidizing composition, or both, contain at least one ceramide compound.

46 Claims, No Drawings

OTHER PUBLICATIONS

Kristi J. Robson et al., "6–Hydroxy–4–sphingenine in human epidermal ceramides", Journal of Lipid Research, vol. 35, 1994, pp. 2060–2068, (1994).
English Language Derwent Abstract of EP 0 736 552.
English Language Derwent Abstract of DE 2 359 399.
English Language Derwent Abstract of FR 2 586 913.
English Language Derwent Abstract of FR 2 673 179.
English Language Derwent Abstract of DE 3 843 892.
English Language Derwent Abstract of DE 4 133 957.
English Language Derwent Abstract of DE 4 424 530.
English Language Derwent Abstract of DE 4 424 533.
English Language Derwent Abstract of DE 4 420 736.
English Language Derwent Abstract of DE 4 402 929.
English Language Derwent Abstract of JP 63–169571.

* cited by examiner

PROCESS FOR DECREASING THE DEGRADATION OF THE COLOR OF OXIDATION DYED KERATIN FIBERS

This application is a 371 of PCT/FR96/01547, filed Oct. 3, 1996.

The present invention relates to a process for dyeing keratin fibers, and in particular human keratin fibres such as the hair, using a dye composition containing at least one oxidation dye and an oxidizing composition containing at least one oxidizing agent, the said dye composition and/or the said oxidizing composition comprising at least one ceramide type compound.

The invention also relates to the dye composition containing at least one oxidation dye and at least one ceramide-type compound used in this process.

Two main types of coloration of keratin fibres exist: direct coloration using direct dyes and/or pigments which are coloured molecules giving the fibres a temporary colour which fades after a few washes, and so-called "oxidation dyeing" coloration using oxidation dye precursors and an oxidizing agent which gives the fibres a fast colour.

In the context of oxidation dyeing, dye compositions are generally used containing oxidation dye precursors, in particular ortho- or para-phenylenediamines, ortho- or para-aminophenols, and heterocyclic compounds, generally known as oxidation bases. Oxidation dye precursors, or oxidation bases, are colourless or weakly coloured compounds which, when combined with oxidizing products, can give rise, by a process of oxidative condensation, to coloured compounds and dyes.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds such as indoline compounds.

The variety of molecules used in oxidation bases and couplers allows a wide variety of colours to be obtained.

As has been seen above, oxidation dyeing allows long-lasting dyeing of the hair; however, it is generally carried out under conditions which result in appreciable degradation of the keratin fibres. The reason for this is that the presence of an oxidizing agent and a generally very alkaline medium results in degradation of the keratin fibres, often making them coarse and brittle.

The so-called "permanent" dyeing obtained with the aid of oxidation dyes should moreover satisfy a certain number of requirements. Thus, it must allow shades to be obtained in the desired intensity and should show good fastness to external agents (light, bad weather, washing, permanent-waving, perspiration, rubbing).

The Applicant has now discovered, entirely surprisingly and unexpectedly, that the use of ceramide-type compounds in compositions for the oxidation dyeing of keratin fibres makes it possible to give these fibres a coloration which shows better resistance over time to the various external attacking factors to which the fibres may be subjected.

This discovery forms the basis of the present invention.

The subject of the present invention is thus a process for dyeing keratin fibres, and in particular human keratin fibres such as the hair, characterized in that the following are applied to these fibres:

at least one dye composition containing, in a medium which is suitable for dyeing, at least one oxidation base chosen from bis(phenyl)alkylenediamines, para-aminophenols, ortho-aminophenols, heterocyclic bases and para-phenylenediamines of formula (I) below, and the addition salts of these compounds with an acid:

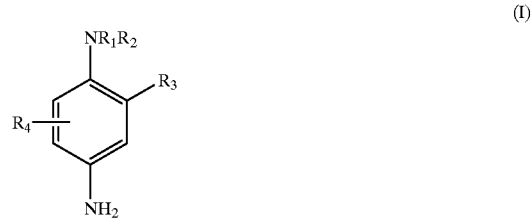

(I)

in which:
R$_1$ represents a hydrogen atom or a C$_1$–C$_4$ alkyl, C$_1$–C$_4$ monohydroxyalkyl, C$_2$–C$_4$ polyhydroxyalkyl, phenyl or 4'-aminophenyl radical,
R$_2$ represents a hydrogen atom or a C$_1$–C$_4$ alkyl, C$_1$–C$_4$ monohydroxyalkyl or C$_2$–C$_4$ polyhydroxyalkyl radical, R$_3$ represents a hydrogen atom, a halogen atom such as a chlorine, bromine, iodine or fluorine atom, or a C$_1$–C$_4$ alkyl, C$_1$–C$_4$ monohydroxyalkyl or C$_1$–C$_4$ hydroxyalkoxy radical,
R$_4$ represents a hydrogen atom or a C$_1$–C$_4$ alkyl radical;
the colour being developed at acidic, neutral or alkaline pH using an oxidizing agent which is added, only at the time of use, to the dye composition or which is present in an oxidizing composition that is applied simultaneously or sequentially in a separate manner;

the said dye composition and/or the said oxidizing composition containing at least one ceramide-type compound.

The colorations obtained according to the dye process in accordance with the invention have excellent resistance properties both with regard to atmospheric agents such as light and bad weather and with regard to perspiration and the various treatments to which the hair may be subjected (washing, permanent-waving). Furthermore, fibres thus dyed are less damaged by the oxidation dyeing process and remain softer and less brittle than when a dyeing process which does not use a ceramide-type compound is used.

According to a particularly preferred embodiment of the dyeing process according to the invention, the dye composition described above is mixed, at the time of use, with an oxidizing composition containing, in a medium which is suitable for dyeing, at least one oxidizing agent present in an amount which is sufficient to develop a coloration. The mixture obtained is then applied to the keratin fibres and is left on them for 3 to 50 minutes approximately, preferably 5 to 30 minutes approximately, after which the fibres are rinsed, washed with shampoo, rinsed again and dried.

The ceramide-type compounds which can be used in the dye composition and/or in the oxidizing composition are known per se. They include ceramides per se, glycoceramides, pseudoceramides and neoceramides, which may be natural or synthetic.

Ceramide-type compounds are described, for example, in patent applications DE-A-4,424,530, DE-A-4,424,533, DE-A-4,402,929, DE-A-4,420,736, WO 95/23807, WO 94/07844, EP-A-0,646,572, WO 95/16665, FR-A-2,673,179, EP-A-0,227,994, WO 94/07844, WO 94/24097 and WO 94/10131, the teachings of which are included herein by way of reference.

The natural or synthetic ceramide-type compounds which can be used according to the present invention preferably correspond to the general formula (II):

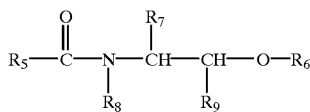

(II)

in which:

R$_5$ denotes:
  either a linear or branched, saturated or unsaturated, C$_5$–C$_{50}$ hydrocarbon radical, it being possible for this radical to be substituted with one or more hydroxyl groups, this or these hydroxyl group(s) optionally being esterified with an acid R$_{10}$COOH, R$_{10}$ being a saturated or unsaturated, linear or branched, optionally mono- or polyhydroxylated C$_1$–C$_{35}$ hydrocarbon radical, it being possible for the hydroxyl group(s) of the radical R$_{10}$ to be esterified with a saturated or unsaturated, linear or branched, optionally mono- or polyhydroxylated C$_1$–C$_{35}$ fatty acid,
  or a radical R"—(NR—CO)—R', in which R denotes a hydrogen atom or a mono- or polyhydroxylated, preferably monohydroxylated C$_1$–C$_{20}$ hydrocarbon radical, R' and R" are hydrocarbon radicals in which the sum of the carbon atoms is between 9 and 30, R' being a divalent radical,
  or a radical R$_{11}$—O—CO—(CH$_2$)$_p$, in which R$_{11}$ denotes a C$_1$–C$_{20}$ hydrocarbon radical, p being an integer ranging from 1 to 12 inclusive;

R$_6$ denotes a hydrogen atom or a (glycosyl)$_n$, (galactosyl)$_m$, sulphogalactosyl, phosphorylethylamine or phosphorylethylammonium radical, in which n is an integer ranging from 1 to 4 inclusive and m is an integer ranging from 1 to 8 inclusive;

R$_7$ denotes a hydrogen atom or a saturated or unsaturated, hydroxylated or non-hydroxylated C$_1$–C$_{33}$ hydrocarbon radical, it being possible for the hydroxyl radical(s) to be esterified with an inorganic acid or with an acid R$_{10}$COOH, R$_{10}$ having the same meanings as those indicated above, it being possible for the hydroxyl radical(s) to be etherified with a (glycosyl)$_n$, (galactosyl)$_m$, sulphogalactosyl, phosphorylethylamine or phosphorylethylammonium radical, it being possible for R$_7$ also to be substituted with one or more C$_1$–C$_1$ alkyl radicals; R$_7$ preferably denotes a C$_{15}$–C$_{26}$ α-hydroxyalkyl radical in which the hydroxyl group can optionally be esterified with a C$_{16}$–C$_{30}$ α-hydroxy acid;

R$_8$ denotes a hydrogen atom, a methyl or ethyl radical, a saturated or unsaturated, linear or branched, optionally hydroxylated C$_3$–C$_{50}$ hydrocarbon radical or a radical —CH$_2$—CHOH—CH$_2$—O—R$_{12}$ in which R$_{12}$ denotes a C$_{10}$–C$_{26}$ hydrocarbon radical or a radical R$_{11}$—O—CO—(CH$_2$)$_p$, R$_{11}$ denoting a C$_1$–C$_{20}$ hydrocarbon radical and p being an integer ranging from 1 to 12 inclusive;

R$_9$ denotes a hydrogen atom or a saturated or unsaturated, linear or branched, optionally mono- or polyhydroxylated C$_1$–C$_{30}$ hydrocarbon radical, it being possible for the hydroxyl radical(s) to be etherified with a (glycosyl)$_n$, (galactosyl)$_m$, sulphogalactosyl, phosphorylethylamine or phosphorylethylammonium radical;

with the proviso that when R$_7$ and R$_9$ denote a hydrogen atom or when R$_7$ denotes a hydrogen atom and R$_9$ denotes a methyl radical, then R$_8$ does not denote a hydrogen atom or a methyl or ethyl radical.

Among the compounds of formula (II) above, the ceramides and/or glycoceramides whose structures are described by Downing in Journal of Lipid Research, Vol. 35, page 2060–2068, 1994, or those described in French patent application FR-2,673,179, and the teachings of which are included herein by way of reference are preferred.

The ceramide-type compounds more particularly preferred according to the invention are compounds of formula (II) in which R$_5$ denotes an optionally hydroxylated, saturated or unsaturated alkyl radical derived from C$_{14}$–C$_{22}$ fatty acids; R$_6$ denotes a hydrogen atom; and R$_7$ denotes an optionally hydroxylated linear, saturated C$_{11}$–C$_{17}$ radical, and preferably a C$_{13}$–C$_{15}$ radical.

Such compounds are, for example:
N-linoleoyldihydrosphingosine,
N-oleoyldihydrosphingosine,
N-palmitoyldihydrosphingosine,
N-stearoyldihydrosphingosine,
N-behenoyldihydrosphingosine,
N-2-hydroxypalmitoyldihydrosphingosine,
N-stearoylphytosphingosine,
N-palmitamidohexadecanediol,
and mixtures of these compounds.

Specific mixtures such as, for example, mixtures of ceramide(s) 2 and ceramide(s) 5 according to the Downing classification can also be used.

The compounds of formula (II) for which R$_5$ denotes a saturated or unsaturated alkyl radical derived from fatty acids; R$_6$ denotes a galactosyl or sulphogalactosyl radical; and R$_7$ denotes a saturated or unsaturated C$_{12}$–C$_{22}$ hydrocarbon radical and preferably a —CH=CH—(CH$_2$)$_{12}$—CH$_3$ group, can also be used.

By way of example, the product consisting of a mixture of glycoceramides, sold under the trade name Glycocer by the company Waitaki International Biosciences may be mentioned.

The compounds of formula (II) described in patent applications EP-A-0,227,994 and WO 94/07844 can also be used.

Such compounds are, for example, Questamide H, also known as bis(N-hydroxyethyl-N-cetyl)malonamide and sold by the company Quest, and cetylic acid N-(2-hydroxyethyl)-N-(3-cetyloxy-2-hydroxypropyl)amide.

N-Docosanoyl-N-methyl-D-glucamine as described in patent application wo 94/24097 can also be used.

Among the bis(phenyl)alkylenediamines which can be used as oxidation bases in the dye composition used in the process of the invention, mention may be made in particular of the compounds corresponding to formula (III) below, and the addition salts thereof with an acid:

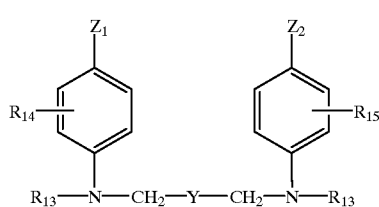

(III)

in which:
  Z$_1$, and Z$_2$, which may be identical or different, represent a hydroxyl radical or a radical NHR$_{16}$ in which R$_{16}$ represents a hydrogen atom or a C$_1$–C$_4$ alkyl radical,
  R$_{13}$ represents a hydrogen atom or a C$_1$–C$_4$ alkyl, C$_1$–C$_4$ monohydroxyalkyl, C$_2$–C$_4$ polyhydroxyalkyl or C$_1$–C$_4$ aminoalkyl radical in which the amino residue can be substituted, $R_{14}$ and $R_{15}$, which may be identical or different, represent a hydrogen or halogen atom or a $C_1$–$C_4$ alkyl radical, Y represents a radical taken from the group consisting of the following radicals:

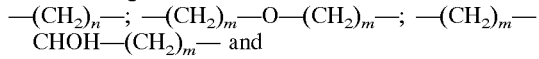

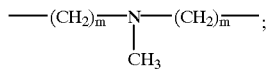

in which n is an integer between 0 and 8 inclusive and m is an integer between 0 and 4 inclusive.

Among the bis(phenyl)alkylenediamines of formula (III) above, mention may be made more particularly of N,N'-bis(β-hydroxyethyl-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, and the addition salts thereof with an acid.

Among these bis(phenyl)alkylenediamines of formula (III), N,N'-bis(β-hydroxyethyl)-N,N'-bis(4'-aminophenyl)-1,3-diaminopropanol or one of the addition salts thereof with an acid is particularly preferred.

Among the para-aminophenols which can be used as oxidation bases in the dye composition used in the process of the invention, mention may be made in particular of the compounds corresponding to formula (IV) below, and the addition salts thereof with an acid:

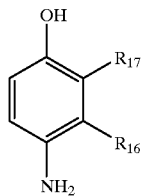

(IV)

in which:

$R_{17}$ represents a hydrogen atom or a $C_1$–$C_4$ alkyl, $C_1$–$C_4$ monohydroxyalkyl, $(C_1$–$C_4)$alkoxy$(C_1$–$C_4)$alkyl, $C_1$–$C_4$ aminoalkyl or hydroxy $(C_1$–$C_4)$ alkylamino $(C_1$–$C_4)$ alkyl radical, $R_{18}$ represents a hydrogen or fluorine atom or a $C_1$–$C_4$ alkyl, $C_1$–$C_4$ monohydroxyalkyl, $C_2$–$C_4$ polyhydroxyalkyl, $C_1$–$C_4$ aminoalkyl, cyano$(C_1$–$C_4)$ alkyl or $(C_1$–$C_4)$alkoxy$(C_1$–$C_4)$alkyl radical, it being understood that at least one of the radicals $R_{17}$ and $R_{18}$ represents a hydrogen atom.

Among the para-aminophenols of formula (IV) above, mention may be made more particularly of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the addition salts thereof with an acid.

Among the ortho-aminophenols which can be used as oxidation bases in the dye composition used in the process of the invention, mention may be made more particularly of 2-aminophenol, 2-amino-5-methylphenol, 2-amino-6-methylphenol and 5-acetamido-2-aminophenol, and the addition salts thereof with an acid.

Among the heterocyclic bases which can be used as oxidation bases in the dye composition used in the process of the invention, mention may be made more particularly of pyridine derivatives, pyrimidine derivatives and pyrazole derivatives, and the addition salts thereof with an acid.

Among the pyridine derivatives, mention may be made more particularly of the compounds described, for example, in GB patents 1,026,978 and 1,153,196, such as 2,5-diaminopyridine, and the addition salts thereof with an acid.

Among the pyrimidine derivatives, mention may be made more particularly of the compounds described, for example, in German patent DE 2,359,399 or Japanese patents JP 88-169,571 and JP 91-333,495, such as 2,4,5,6-tetraaminopyrimidine and 4-hydroxy-2,5,6-triaminopyrimidine, and the addition salts thereof with an acid.

Among the pyrazole derivatives, mention may be made more particularly of the compounds described in patents DE 3,843,892 and DE 4,133,957 and patent applications WO 94/08969 and WO 94/08970 such as 4,5-diamino-1-methylpyrazole, 3,4-diaminopyrazole and 4,5-diamino-1-(4'-chlorobenzyl)pyrazole, and the addition salts thereof with an acid.

Among the paraphenylenediamines of formula (I) above, mention may be made more particularly of para-phenylenediamine, para-toluylenediamine, 2-chloro-paraphenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N, N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-3-methylaniline, 4-amino-3-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl, β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine and 2-β-hydroxyethyloxy-para-phenylenediamine, and the addition salts thereof with an acid.

Among the para-phenylenediamines of formula (I) above, para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine and 2-chloro-para-phenylenediamine, and the addition salts thereof with an acid, are most particularly preferred.

The ceramide-type compound(s) preferably represent(s) from 0.0001% to 10% by weight approximately relative to the total weight of the dye composition or relative to the total weight of the oxidizing composition, and even more preferably from 0.001% to 5% by weight approximately.

The oxidation base(s) preferably represent(s) from 0.0001 to 20% by weight approximately relative to the total weight of the dye composition, and even more preferably from 0.005 to 10% by weight approximately.

The dye compositions used in the dyeing process of the invention also generally contain one or more couplers chosen from the compounds usually used in this respect in oxidation dyeing, and among which mention may be made of meta-diphenols, meta-aminophenols, meta-phenylenediamines, mono- or polyhydroxylated naphthalene derivatives, sesamol and its derivatives, heterocyclic compounds such as, for example, pyridine couplers and indole couplers, and addition salts thereof with an acid.

When they are present, the coupler(s) preferably represent(s) from 0.0005% to 20% by weight approximately relative to the total weight of the dye composition, and even more preferably from 0.01% to 10% by weight approximately.

The addition salts with an acid which can be used in the context of the dye compositions used in the process of the invention (para-phenylenediamines of formula (I), bis(phenyl)alkylenediamines, para-aminophenols, ortho-aminophenols, heterocyclic bases and couplers) are chosen in particular from the hydrochlorides, hydrobromides, sulphates and tartrates.

The medium which is suitable for dyeing (or the support) for the dye compositions used in the dyeing process in accordance with the invention generally consists of water or a mixture of water and at least one organic solvent for dissolving the compounds which would not be sufficiently soluble in water. As organic solvent, mention may be made, for example, of $C_1$–$C_4$ lower alkanols, such as ethanol and isopropanol; glycerol; glycols and glycol ethers such as 2-butoxyethanol, propylene glycol, propylene glycol monomethyl ether, diethylene glycol monoethyl ether and monomethyl ether, and aromatic alcohols such as benzyl alcohol or phenoxyethanol, similar products and mixtures thereof.

The solvents can be present in proportions preferably of between 1 and 40% by weight approximately relative to the total weight of the dye composition, and even more preferably between 5 and 30% by weight approximately.

The pH of the dye composition used in the dyeing process in accordance with the invention is generally between 3 and 11.5, and even more preferably between 7 and 11. It can be adjusted to the desired value using acidifying or basifying agents usually used in the dyeing of keratin fibres.

Among the acidifying agents, mention may be made, by way of example, of inorganic or organic acids such as hydrochloric acid and orthophosphoric acid, carboxylic acids such as tartaric acid, citric acid and lactic acid, and sulphonic acids.

Among the basifying agents, mention may be made, by way of example, of aqueous ammonia, alkaline carbonates, alkanolamines such as mono-, di- and triethanolamines and derivatives thereof, sodium hydroxide, potassium hydroxide and compounds of formula (V) below:

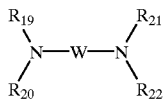

(V)

in which W is a propylene residue optionally substituted with a hydroxyl group or a $C_1$–$C_4$ alkyl radical; $R_{19}$, $R_{20}$, $R_{21}$ and $R_{22}$, which may be identical or different, represent a hydrogen atom or a $C_1$–$C_4$ alkyl or $C_1$–$C_4$ hydroxyalkyl radical.

The dye composition used in the dyeing process in accordance with the invention can also contain, in addition to the dyes defined above, direct dyes, in particular in order to modify the shades or to enrich them with glints.

The dye composition used in the dyeing process of the invention can also contain various adjuvants conventionally used in compositions for dyeing the hair, such as anionic, cationic, nonionic, amphoteric or zwitteronic surfactants or mixtures thereof, anionic, cationic, nonionic, amphoteric or zwitteronic polymers or mixtures thereof, inorganic or organic thickeners, antioxidants, penetration agents, sequestering agents, fragrances, buffers, dispersing agents, conditioners such as, for example, silicones, film-forming agents, preserving agents and opacifiers.

Needless to say, a person skilled in the art will take care to select this or these optional complementary compounds such that the advantageous properties intrinsically associated with the dyeing process in accordance with the invention are not, or are not substantially, adversely affected by the addition(s) envisaged.

The dye composition used in the dyeing process of the invention can be in various forms, such as in the form of liquids, creams or gels or in any other form which is suitable for dyeing keratin fibres, and in particular human hair.

The oxidizing agent present in the oxidizing composition used in the dyeing process of the invention can be chosen from the oxidizing agents conventionally used for the oxidation dyeing of keratin fibres, and among which mention may be made of hydrogen peroxide, urea peroxide, alkali metal bromates and persalts such as perborates and persulphates. Hydrogen peroxide is particularly preferred.

The pH of the oxidizing composition containing the oxidizing agent as defined above is such that, after mixing with the dye composition, the pH of the resulting composition applied to the keratin fibres preferably ranges between 3 and 12 approximately and even more preferably between 5 and 11. It is adjusted to the desired value using acidifying or basifying agents usually used in the dyeing of keratin fibres and as defined above.

The oxidizing composition as defined above can also contain various adjuvants conventionally used in compositions for dyeing hair, and as defined above.

The composition as finally applied to the keratin fibres can be in various forms, such as in the form of liquids, creams or gels or in any other form which is suitable for dyeing keratin fibres, and in particular human hair.

The dye composition used in the process of the invention and containing at least one oxidation base and at least one compound of ceramide type as described above is novel and also constitutes a subject of the invention.

Another subject of the invention is a multi-compartment dyeing device or "kit" or any other multi-compartment packaging system, a first compartment of which contains the dye composition as defined above and a second compartment of which contains the oxidizing composition as defined above. These devices can be equipped with means which allow the desired mixture to be applied to the hair, such as the devices described in patent FR-2,586,913 in the name of the Applicant.

The examples which follow are intended to illustrate the invention without, however, limiting its scope.

EXAMPLES

Comparative Examples 1 and 2

The following dye compositions were prepared (contents in grams):

| EXAMPLE | 1(*) | 2 |
|---|---|---|
| Para-phenylenediamine | 0.108 | 0.108 |
| Meta-aminophenol | 0.109 | 0.109 |
| N-Oleoyldihydrosphingosine (ceramide) | 0 | 2.5 |
| Common dye support | () | () |
| Demineralized water q.s. | 100 g | 100 g |

(*): composition not forming part of the invention
(**): Common dye support:

| | |
|---|---|
| Cetyl alcohol and stearyl alcohol as a 50/50 mixture | 18 g |
| 2-Octyldodecanol | 3 g |
| Cetylstearyl alcohol oxyethylenated with 15 mol of ethylene oxide | 3 g |
| Ammonium lauryl sulphate containing 30% acitve material (A.M.) | 12 g |
| Aqueous solution containing 60% A.M. of a cationic polymer having the following repeating unit: | 3 g A.M. |

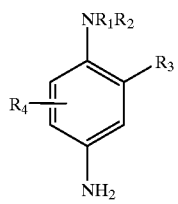

| | |
|---|---|
| Aqueous ammonia containing 20% $NH_3$ | 12 g |
| Ammonium thiolactate (containing 50 eq. % of thiolactic acid) | 0.8 g |

At the time of use, each dye composition was mixed with one-and-a-half times its weight of 20-volumes aqueous hydrogen peroxide solution (6% by weight).

Each resulting composition was applied for 30 minutes to locks of natural grey hair containing 90% white hairs. The locks of hair were then rinsed, washed with a standard shampoo and then dried.

The locks of hair thus dyed then underwent a test of resistance to bad weather. The aim of this test was to evaluate the degradation of the coloration under the simultaneous action of light (Xenotest) and soft water.

To do this, the locks of dyed hair were fixed on a support (cardboard or plastic). These supports were arranged on sample holders which were rotated about a xenon lamp for a period of 64 hours under a relative moisture content of 60% and at a temperature of 42.5±2.5° C. During these 64 hours, the action of the light was interrupted every 12 hours, in order to subject the locks to a cold rain for a period of 30 minutes.

The colour of the locks was evaluated in the Munsell system, before and after the bad-weather resistance test, using a Minolta CM 2002 calorimeter.

According to the Munsell notation, a colour is defined by the expression H V/C in which the three parameters respectively denote the shade or Hue (H), the intensity or Value (V) and the purity or Chromaticity (C), the oblique line in this expression simply being a convention and not indicating a ratio.

The difference in colour of each lock before and after the light-fastness test reflects the degradation of the coloration due to the action of light and was calculated by applying the Nickerson formula:

$$\Delta E = 0.4 \, Co\Delta H + 6\Delta V + 3\Delta C$$

as described, for example, in "Couleur, Industrie et Technique"; pages 14–17; Vol. No. 5; 1978.

In this formula, ΔE represents the difference in colour between two locks, ΔH, ΔV and ΔC represent the variation in absolute value of the parameters H, V and C, and Co represents the purity of the lock relative to which it is desired to evaluate the difference in colour (purity of the lock before the test).

The results are given in Table II below:

TABLE II

| | Colour before the test | Colour after the test | Degradation of the coloration | | | |
|---|---|---|---|---|---|---|
| EXAMPLE | | | ΔH | ΔV | ΔC | ΔE |
| 1(*) | 5.2 R 3.2/2.5 | 9.85 YR 5.5/2.7 | 14.65 | 2.3 | 0.2 | 29 |
| 2 | 5.4 R 3.7/2.7 | 9.05 YR 4.3/2.7 | 13.4 | 0.6 | 0 | 18.1 |

(*): example not forming part of the invention

These results show that composition 1 not forming part of the invention, since it contains no ceramide, leads to a coloration on the hair which is much less resistant to the action of bad weather than the coloration obtained with composition 2 in accordance with the invention, i.e. the composition containing a ceramide.

What is claimed is:

1. A process for decreasing the degradation of the color of keratin fibers dyed according to an oxidation dyeing process comprising:

(a) applying to said fibers at least one dye composition containing, in a medium suitable for dyeing, at least one oxidation base selected from bis(phenyl) alkylenediamines, para-aminophenols, ortho-aminophenols, heterocyclic bases and para-phenylenediamines of formula (I), and the addition salts of these compounds with an acid:

(I)

$$\begin{array}{c}NR_1R_2\\ \\R_4\!\!-\!\!\!\bigcirc\!\!-\!\!R_3\\ \\NH_2\end{array}$$

in which:
$R_1$ represents a hydrogen atom or a $C_1$–$C_4$ alkyl, $C_1$–$C_4$ monohydroxyalkyl, $C_2$–$C_4$ polyhydroxyalkyl, phenyl or 4'-aminophenyl radical,
$R_2$ represents a hydrogen atom or a $C_1$–$C_4$ alkyl, $C_1$–$C_4$ monohydroxyalkyl or $C_2$–$C_4$ polyhydroxyalkyl radical,
$R_3$ represents a hydrogen atom, a halogen atom, or a $C_1$–$C_4$ alkyl, $C_1$–$C_4$ monohydroxyalkyl or $C_1$–$C_4$ hydroxyalkoxy radical, and
$R_4$ represents a hydrogen atom or a $C_1$–$C_4$ alkyl radical; and (b) developing the colour at acidic, neutral or alkaline pH using an oxidizing agent, wherein said oxidizing agent is added to said dye composition at the time of use or is present in an oxidizing composition applied simultaneously or sequentially in a separate manner from said dye composition;

wherein said dye composition, said oxidizing composition, or both, contain at least one ceramide compound.

2. A process according to claim 1, wherein said keratin fiber is human hair.

3. A process according to claim 1, wherein $R_3$ represents a chlorine, bromine, iodine or fluorine atom.

4. A process according to claim 1, wherein said dye composition is mixed, at the time of use, with an oxidizing composition containing, in a medium suitable for dyeing, at least one oxidizing agent present in an amount sufficient to develop a coloration.

5. A process according to claim 1, wherein said at least one ceramide compound is selected from natural or synthetic molecules selected from formula (II):

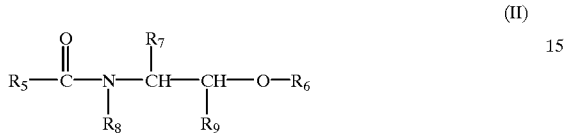

(II)

in which:

$R_5$ denotes:
   a linear or branched, saturated or unsaturated, $C_5$–$C_{50}$ hydrocarbon radical, optionally substituted with at least one hydroxyl group and said at least one hydroxyl group being optionally esterified with an acid $R_{10}COOH$, wherein $R_{10}$ is a saturated or unsaturated, linear or branched, optionally mono- or polyhydroxylated $C_1$–$C_{35}$ hydrocarbon radical, it being possible for said at least one hydroxyl group of the radical $R_{10}$ to be esterified with a saturated or unsaturated, linear or branched, optionally mono- or polyhydroxylated $C_1$–$C_{35}$ fatty acid, or
   a radical R"—(NR—CO)—R', in which R denotes a hydrogen atom or a mono- or polyhydroxylated $C_1$–$C_{20}$ hydrocarbon radical, and R' and R" are hydrocarbon radicals in which the sum of the carbon atoms ranges from 9 to 30, R' being a divalent radical, or
   a radical $R_{11}$—O—CO—$(CH_2)_p$, in which $R_{11}$ denotes a $C_1$–$C_{20}$ hydrocarbon radical and p is an integer ranging from 1 to 12;

$R_6$ denotes a hydrogen atom or a $(glycosyl)_n$, $(galactosyl)_m$, sulphogalactosyl, phosphorylethylamine or phosphorylethylammonium radical, wherein n is an integer ranging from 1 to 4 and m is an integer ranging from 1 to 8;

$R_7$ denotes a hydrogen atom or a saturated or unsaturated, hydroxylated or non-hydroxylated $C_1$–$C_{33}$ hydrocarbon radical, wherein said hydroxyl radical is optionally esterified with an inorganic acid or with an acid $R_{10}COOH$, wherein $R_{10}$ is a saturated or unsaturated, linear or branched, optionally mono- or polyhydroxylated $C_1$–$C_{35}$ hydrocarbon radical, it being possible for the hydroxyl group(s) of $R_{10}$ to be esterified with a saturated or unsaturated, linear or branched, optionally mono- or polyhydroxylated $C_1$–$C_{35}$ fatty acid, it being possible for the hydroxyl radical(s) to be etherified with a a $(glycosyl)_n$, $(galactosyl)_m$, sulphogalactosyl, phosphorylethylamine or phosphorylethylammoniurn radical, wherein n is an integer ranging from 1 to 4 and m is an integer ranging from 1 to 8, it also being possible for $R_7$ to be substituted with one or more $C_1$–$C_{14}$ alkyl radicals;

$R_8$ denotes a hydrogen atom, a methyl or ethyl radical or a saturated or unsaturated, linear or branched, optionally hydroxylated $C_3$–$C_{50}$ hydrocarbon radical or a radical —$CH_2$—CHOH—$CH_2$—O—$R_{12}$ in which $R_{12}$ denotes a $C_{10}$–$C_{26}$ hydrocarbon radical or a radical $R_{11}$—O—CO—$(CH_2)_p$, $R_{11}$ denoting a $C_1$–$C_{20}$ hydrocarbon radical and p being an integer ranging from 1 to 12;

$R_9$ denotes a hydrogen atom or a saturated or unsaturated, linear or branched, optionally mono- or polyhydroxylated $C_1$–$C_{30}$ hydrocarbon radical, optionally wherein the hydroxy radical(s) is etherified with a $(glycosyl)_n$, $(galactosyl)_m$, sulphogalactosyl, phosphorylethylamine or phosphorylethylammonium radical, wherein n is an integer ranging from 1 to 4 and m is an integer ranging from 1 to 8; wherein when $R_7$ and $R_9$ denote a hydrogen atom or when $R_7$ denotes a hydrogen atom and $R_9$ denotes a methyl radical, then $R_8$ does not denote a hydrogen atom or a methyl or ethyl radical.

6. A process according to claim 5, wherein R in said radical R"—(NR—CO)—R' denotes a monohydroxylated $C_1$–$C_{20}$ hydrocarbon radical.

7. A process according to claim 5, wherein $R_7$ denotes a $C_{15}$–$C_{26}$ α-hydroxyalkyl radical in which the hydroxyl group is optionally esterified with a $C_{16}$–$C_{30}$ α-hydroxy acid.

8. A process according to claim 5, wherein said at least one ceramide-type compound is selected from compounds of formula (II) in which $R_5$ denotes an optionally hydroxylated, saturated or unsaturated alkyl radical derived from $C_{14}$–$C_{22}$ fatty acids; $R_6$ denotes a hydrogen atom; and $R_7$ denotes an optionally hydroxylated linear, saturated $C_{11}$–$C_{17}$ radical.

9. A process according to claim 1, wherein said at least one ceramide is selected from:
   N-linoleoyldihydrosphingosine,
   N-oleoyldihydrosphingosine,
   N-palmitoyldihydrosphingosine,
   N-stearoyldihydrosphingosine,
   N-behenoyldihydrosphingosine,
   N-2-hydroxypalmitoyldihydrosphingosine,
   N-stearoylphytosphingosine, and
   N-palmitamidohexadecanediol.

10. A process according to claim 5 wherein said at least one ceramide is selected from compounds of formula (II) in which
   $R_5$ denotes a saturated or unsaturated alkyl radical derived from fatty acids;
   $R_6$ denotes a galactosyl or sulphogalactosyl radical; and
   $R_7$ denotes a saturated or unsaturated $C_{12}$–$C_{22}$ hydrocarbon radical.

11. A process according to claim 10, wherein $R_7$ denotes a —CH=CH—$(CH_2)_{12}$—$CH_3$ group.

12. A process according to claim 1, wherein said bis (phenyl)alkylenediamines are selected from compounds of formula (III), and the addition salts thereof with an acid:

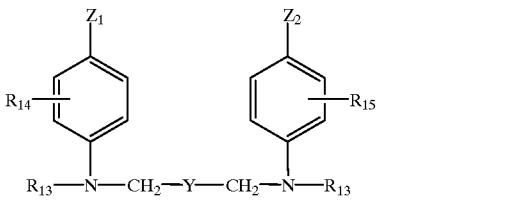

(III)

in which:

$Z_1$ and $Z_2$ independently represent a hydroxyl radical or a radical $NHR_{16}$ in which $R_{16}$ represents a hydrogen atom or a $C_1$–$C_4$ alkyl radical, $R_{13}$ independently represents a hydrogen atom or a $C_1$–$C_4$ alkyl, $C_1$–$C_4$ monohydroxyalkyl, $C_2$–$C_4$ polyhydroxyalkyl or $C_1$–$C_4$ aminoalkyl radical in which the amino residue can be substituted, $R_{14}$ and $R_{15}$ independently represent a hydrogen or halogen atom or a $C_1$–$C_4$ alkyl radical, Y represents a radical selected from:

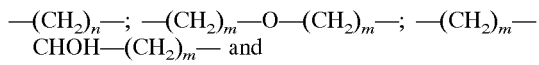

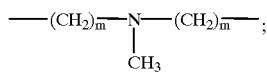

in which:
n is an integer ranging from 0 to 8, and
m is an integer ranging from 0 to 4.

13. A process according to claim 12, wherein said bis(phenyl)alkylenediamines of formula (III) are selected from N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, and the addition salts thereof with an acid.

14. A process according to claim 1 wherein said para-aminophenols are selected from compounds of formula (IV), and the addition salts thereof with an acid:

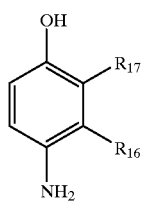

(IV)

in which:
$R_{17}$ represents a hydrogen atom or a $C_1$–$C_4$ alkyl, $C_1$–$C_4$ monohydroxyalkyl, $(C_1$–$C_4)$alkoxy$(C_1$–$C_4)$alkyl, $C_1$–$C_4$ aminoalkyl or hydroxy$(C_1$–$C_4)$alkylamino $(C_1$–$C_4)$alkyl radical, $R_{18}$ represents a hydrogen or fluorine atom or a $C_1$–$C_4$ alkyl, $C_1$–$C_4$ monohydroxyalkyl, $C_2$–$C_4$ polyhydroxyalkyl, $C_1$–$C_4$ aminoalkyl, cyano$(C_1$–$C_4)$ alkyl or $(C_1$–$C_4)$alkoxy$(C_1$–$C_4)$alkyl radical, wherein at least one of the radicals $R_{17}$ and $R_{18}$ represents a hydrogen atom.

15. A process according to claim 14, wherein said para-aminophenols are selected from para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol and 4-amino-2-(β-hydroxyethylaminomethyl)phenol, and the addition salts thereof with an acid.

16. A process according to claim 1, wherein said ortho-aminophenols are selected from 2-aminophenol, 2-amino-5-methylphenol, 2-amino-6-methylphenol and 5-acetamido-2-aminophenol, and the addition salts thereof with an acid.

17. A process according to claim 1, wherein said heterocyclic bases are selected from pyridine compounds, pyrimidine compounds and pyrazole compounds, and the addition salts thereof with an acid.

18. A process according to claim 17, wherein said heterocyclic bases are selected from 2,4,5,6-tetraaminopyrimidine, 2,5-diaminopyridine, 4,5-diamino-1-methylpyrazole, 3,4-diaminopyrazole, 4,5-diamino-1-(4'-chlorobenzyl)pyrazole and 4-hydroxy-2,5,6-triaminopyrimidine, and the addition salts thereof with an acid.

19. A process according to claim 1, wherein said para-phenylenediamines of formula (I) are selected from para-phenylenediamine, para-toluylenediamine, 2-chloro-paraphenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-3-methylaniline, 4-amino-3-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl, β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine and 2-β-hydroxyethyloxy-para-phenylenediamine, and the addition salts thereof with an acid.

20. A process according to claim 19, wherein said para-phenylenediamines are selected from para-phenylenediamine, para-toluylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine and 2-chloro-para-phenylenediamine, and the addition salts thereof with an acid.

21. A process according to claim 1, wherein said at least one ceramide compound is present in an amount ranging from 0.0001% to 10% by weight relative to the total weight of said dye composition or relative to the total weight of said oxidizing composition.

22. A process according to claim 21, wherein said at least one ceramide compound is present in an amount ranging from 0.001% to 5% by weight relative to the total weight of said dye composition or relative to the total weight of said oxidizing composition.

23. A process according to claim 1, wherein said at least one oxidation base is present in an amount ranging froms 0.0001 to 20% by weight relative to the total weight of said dye composition.

24. A process according to claim 23, wherein said at least one oxidation base is present in an amount ranging from 0.005 to 10% by weight relative to the total weight of said dye composition.

25. A process according to claim 1, wherein said dye composition further comprises at least one coupler.

26. A process according to claim 25, wherein said at least one coupler is selected from meta-diphenols, meta-aminophenols, meta-phenylenediamines, mono- and polyhydroxylated naphthalene compounds, sesamol compounds, heterocyclic compounds, and the addition salts thereof with an acid.

27. A process according to claim 26, wherein said heterocyclic compounds are selected from pyridine couplers and indole couplers.

28. A process according to claim 25, wherein said at least one coupler is present in an amount ranging from 0.0005% to 20% by weight relative to the total weight of said dye composition.

29. A process according to claim 28, wherein said at least one coupler is present in an amount ranging from 0.01% to 10% by weight relative to the total weight of said dye composition.

30. A process according to claim 1, wherein said addition salts with an acid are selected from hydrochlorides, hydrobromides, sulphates and tartrates.

31. A process according to claim 1, wherein said medium suitable for dyeing comprises water or a mixture of water and at least one organic solvent.

32. A process according to claim 31, wherein said at least one organic solvent is selected from $C_1$–$C_4$ lower alkanols, glycerol, glycols and glycol ethers, and aromatic alcohols.

33. A process according to claim 31, wherein said medium suitable for dyeing comprises water and at least one organic solvent, and said at least one organic solvent is present in an amount ranging from 1 to 40% by weight, relative to the total weight of said dye composition.

34. A process according to claim 33, wherein said at least one organic solvent is present in an amount ranging from 5 to 30% by weight, relative to the total weight of said dye composition.

35. A process according to claim 1, wherein said dye composition has a pH ranging from 3 to 11.5.

36. A process according to claim 35, wherein said dye composition has a pH ranging from 7 to 11.

37. A process according to claim 1, wherein said oxidizing agent is selected from hydrogen peroxide, urea peroxide, alkali metal bromates and persalts.

38. A process according to claim 37, wherein said persalts are selected from perborates and persulphates.

39. A process according to claim 37, wherein said oxidizing agent is hydrogen peroxide.

40. A process according to claim 1 wherein said dye composition is in the form of a liquid, a cream, a gel, or any form suitable for dyeing keratin fiber.

41. A composition for the oxidation dyeing of a keratin fiber comprising, in a medium suitable for dyeing:

at least one oxidation base selected from bis(phenyl) alkylenediamines, para-aminophenols, orthoaminophenols, heterocyclic bases and para-phenylenediamines of formula (I), and the addition salts of these compounds with an acid:

(I)

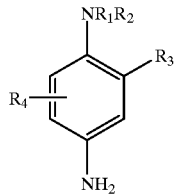

in which:

$R_1$ represents a hydrogen atom or a $C_1$–$C_4$ alkyl, $C_1$–$C_4$ monohydroxyalkyl, $C_2$–$C_4$ polyhydroxyalkyl, phenyl or 4'-aminophenyl radical, $R_2$ represents a hydrogen atom or a $C_1$–$C_4$ alkyl, $C_1$–$C_4$ monohydroxyalkyl or $C_2$–$C_4$ polyhydroxyalkyl radical, $R_3$ represents a hydrogen atom, a halogen atom, or a $C_1$–$C_4$ alkyl, $C_1$–$C_4$ monohydroxyalkyl or $C_1$–$C_4$ hydroxyalkoxy radical, $R_4$ represents a hydrogen atom or a $C_1$–$C_4$ alkyl radical; and at least one ceramide compound.

42. A composition according to claim 41, wherein said keratin fiber is human hair.

43. A composition according to claim 41, wherein $R_3$ represents a chlorine, bromine, iodine or fluorine atom.

44. A multi-compartment device or multi-compartment dyeing kit comprising:

a first compartment containing a dye composition containing, in a medium suitable for dyeing, at least one oxidation base selected from bis(phenyl) alkylenediamines, para-aminophenols, orthoaminophenols, heterocyclic bases and para-phenylenediamines of formula (I), and the addition salts of these compounds with an acid:

(I)

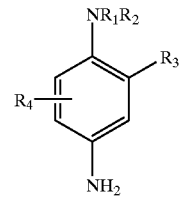

in which:

$R_1$ represents a hydrogen atom or a $C_1$–$C_4$ alkyl, $C_1$–$C_4$ monohydroxyalkyl, $C_2$–$C_4$ polyhydroxyalkyl, phenyl or 4'-aminophenyl radical, $R_2$ represents a hydrogen atom or a $C_1$–$C_4$ alkyl, $C_1$–$C_4$ monohydroxyalkyl or $C_2$–$C_4$ polyhydroxyalkyl radical, $R_3$ represents a hydrogen atom, a halogen atom, or a $C_1$–$C_4$ alkyl, $C_1$–$C_4$ monohydroxyalkyl or $C_1$–$C_4$ hydroxyalkoxy radical, $R_4$ represents a hydrogen atom or a $C_1$–$C_4$ alkyl radical; and a second compartment containing at least one oxidizing composition; wherein said dye composition and/or said oxidizing composition contains at least one ceramide compound.

45. A multi-compartment device or multi-compartment dyeing kit according to claim 44, wherein $R_3$ represents a chlorine, bromine, iodine or fluorine atom.

46. A process according to claim 8, wherein $R_7$ denotes an optionally hydroxylated linear, saturated $C_{13}$–$C_{15}$ radical.

* * * * *

UNITED STATES PATENT AND TRADEMARK OFFICE
CERTIFICATE OF CORRECTION

PATENT NO.    : 6,251,378 B1
DATED         : June 26, 2001
INVENTOR(S)   : Laurent et al.

Page 1 of 1

It is certified that error appears in the above-identified patent and that said Letters Patent is hereby corrected as shown below:

Title page,
Item [75], Inventors, line 1, "Asniéres" should read -- Asnières --.
Item [73], Assignee, "L'Oreal" should read -- L'Oréal --.

Column 11,
Line 59, "a a $(glycosyl)_n$," should read -- a $(glycosyl)_n$, --.
Line 60, "phosphorylethylammoniurn" should read -- phosphorylethylammonium --.

Column 13,
Line 35, in the structure for formula (IV) that appears after "with an acid:",
"$R_{16}$" should read -- $R_{18}$ --.

Column 14,
Line 57, "ranging froms" should read -- ranging from --.

Signed and Sealed this

Twenty-third Day of April, 2002

JAMES E. ROGAN
*Director of the United States Patent and Trademark Office*